(12) United States Patent  
Krafthefer et al.

(10) Patent No.: US 8,151,626 B2
(45) Date of Patent: Apr. 10, 2012

(54) SYSTEM AND METHOD FOR SENSING HIGH TEMPERATURE PARTICULATE MATTER

(75) Inventors: Brian C. Krafthefer, Stillwater, MN (US); Gregory E. Stewart, North Vancouver (CA); Jeff Boehler, Morristown, NJ (US); Matthew Below, Morristown, NJ (US); Michael L. Rhodes, Richfield, MN (US)

(73) Assignee: Honeywell International Inc., Morristown, NJ (US)

( * ) Notice: Subject to any disclaimer, the term of this patent is extended or adjusted under 35 U.S.C. 154(b) by 599 days.

(21) Appl. No.: 12/265,583

(22) Filed: Nov. 5, 2008

(65) Prior Publication Data

US 2010/0107737 A1 May 6, 2010

Related U.S. Application Data

(60) Provisional application No. 60/985,572, filed on Nov. 5, 2007.

(51) Int. Cl.
*G01N 15/06* (2006.01)
*B01D 46/02* (2006.01)
*F01N 11/00* (2006.01)

(52) U.S. Cl. ............... 73/28.01; 73/28.04; 73/31.05
(58) Field of Classification Search .......... 73/23.31, 73/28.01, 28.04, 31.05, 31.02, 31.03
See application file for complete search history.

(56) References Cited

U.S. PATENT DOCUMENTS

| | | | |
|---|---|---|---|
| 4,021,326 A | 5/1977 | Pollner et al. | |
| 4,152,234 A | 5/1979 | Pollner | |
| 4,300,990 A | 11/1981 | Maurer | |
| 4,307,061 A | 12/1981 | Sarholz | |
| 4,339,320 A | 7/1982 | Friese et al. | |
| 4,485,794 A | 12/1984 | Kimberley et al. | |
| 4,656,832 A | 4/1987 | Yukihisa et al. | |
| 5,076,237 A | 12/1991 | Hartman et al. | |
| 5,180,983 A | 1/1993 | Murata et al. | |
| 5,271,821 A | 12/1993 | Ogasawara et al. | |
| 5,334,932 A * | 8/1994 | Nielsen | 324/204 |
| 5,681,986 A | 10/1997 | Merk et al. | |
| 5,889,196 A | 3/1999 | Ueno et al. | |
| 5,898,257 A | 4/1999 | Sequerra et al. | |
| 6,067,843 A | 5/2000 | Hafele et al. | |
| 6,192,740 B1 | 2/2001 | Thomas et al. | |
| 6,341,501 B2 | 1/2002 | Sugimoto et al. | |
| 6,432,168 B2 | 8/2002 | Schonauer | |

(Continued)

OTHER PUBLICATIONS

Quinn, D.B. et al., "II.C Enabling Technologies—II.C.1 NOx Sensor for Direct Injection Emission Control", FY2005 Progress Report—Advanced Combustion Engine Technologies, (2005), pp. 243-247.*

(Continued)

*Primary Examiner* — Daniel Larkin
(74) *Attorney, Agent, or Firm* — Schwegman, Lundberg & Woessner P.A.

(57) ABSTRACT

Sensor apparatus includes a housing, a probe mounted to the housing, the probe including an elongate first part and a helical coil second part conductively coupled to each in series with first and second terminals at opposite ends thereof, the probe to be inserted into an exhaust stream in an exhaust corridor; and a circuit coupled to the first and second terminals of the sensor probe, to selectively operate the probe as a temperature sensor in a first mode and as a PM sensor in a second mode.

20 Claims, 15 Drawing Sheets

U.S. PATENT DOCUMENTS

| | | |
|---|---|---|
| 6,466,022 B1 | 10/2002 | Koopmans |
| 6,512,375 B1 | 1/2003 | Yamada et al. |
| 6,583,539 B1 | 6/2003 | Zamora |
| 6,601,464 B1 | 8/2003 | Downing |
| 6,634,210 B1 | 10/2003 | Bosch et al. |
| 6,849,238 B2 | 2/2005 | Weyl et al. |
| 6,948,353 B2 | 9/2005 | Toguchi et al. |
| 6,949,874 B2 | 9/2005 | Schumann |
| 6,971,258 B2 | 12/2005 | Rhodes et al. |
| 7,155,334 B1 | 12/2006 | Stewart et al. |
| 7,275,415 B2 | 10/2007 | Rhodes et al. |
| 7,389,773 B2 | 6/2008 | Stewart et al. |
| 2001/0051108 A1 | 12/2001 | Schonauer |
| 2006/0016246 A1 | 1/2006 | Rhodes et al. |
| 2006/0137346 A1 | 6/2006 | Stewart et al. |
| 2007/0039589 A1 | 2/2007 | Stewart et al. |
| 2007/0089399 A1 | 4/2007 | Rhodes et al. |
| 2007/0137177 A1 | 6/2007 | Kittelson et al. |
| 2007/0142999 A1 | 6/2007 | Baramov et al. |
| 2008/0265870 A1 | 10/2008 | Nair et al. |
| 2009/0035870 A1 | 2/2009 | Ruiz |
| 2009/0056416 A1 | 3/2009 | Nair et al. |
| 2009/0113983 A1 | 5/2009 | Krafthefer |
| 2009/0301058 A1* | 12/2009 | Boehler et al. .......... 60/276 |

OTHER PUBLICATIONS

Lawless, W.N. et al., "II.C Enabling Technologies—II.C.2 Small, Inexpensive Combined NOx and O2 Sensor", FY2005 Progress Report—Advanced Combustion Engine Technologies, (2005), pp. 244-251.*

Rhodes, M. et al., "II.C Enabling Technologies—II.C.3 Particulate Matter Sensor for Diesel Engine Soot Control", FY2005 Progress Report—Advanced Combustion Engine Technologies, (2005), pp. 252-255.*

Mendler, C. et al., "II.C Enabling Technologies—II.C.4 Variable Compression Ratio Engine", FY2005 Progress Report—Advanced Combustion Engine Technologies, (2005), pp. 256-258.*

* cited by examiner

SYSTEM AND METHOD FOR SENSING HIGH TEMPERATURE PARTICULATE MATTER

CROSS-REFERENCE TO RELATED APPLICATIONS

This application claims priority under 35 U.S.C. 119(e) to U.S. Provisional Patent Application Ser. No. 60/985,572, filed Nov. 5, 2007; which application is incorporated herein by reference and made a part hereof.

TECHNICAL FIELD

Various embodiments described herein relate to apparatus, systems and methods associated with sensors, including the operation and manufacture of sensors to sense high-temperature particulate matter.

BACKGROUND

Particulate matter sensors are used in internal combustion engines to monitor exhaust characteristics. There is a need for apparatus systems and methods that provide improved reliability and operability of particulate matter sensors particularly with respect to soot that results from incomplete combustion.

Typically, three types of particulate emissions can emit from unburned liquid fuel. A first type particulate includes the unburned or partially burned hydrocarbons, which are sometimes referred to as white smoke. A second type of particulate is soot, a particulate ash, which forms during gas-phase combustion. A third type of particulate is referred to as coke, which is also a particulate ash that forms during liquid-phase combustion.

DETAILED DESCRIPTION

To address the challenges described above, various embodiments described herein may operate to provide an improved particulate matter sensor. Some embodiments of a particulate matter (PM) sensor include a reheating capability to sublimate carbonaceous material that may have deposited thereon or to form a dielectric coating thereon. The PM sensor may be configured with other PM sensors as a PM classifier such as in an exhaust stream. The PM sensor may be articulated into and out of an exhaust stream for various applications. The PM sensor may be coupled with a diesel particulate filter (DPF) and configured within an exhaust stream and upstream from a turbine in a turbine-compressor arrangement. A DPF may be configured that can detect localized failure of the DPF.

Figure 1:
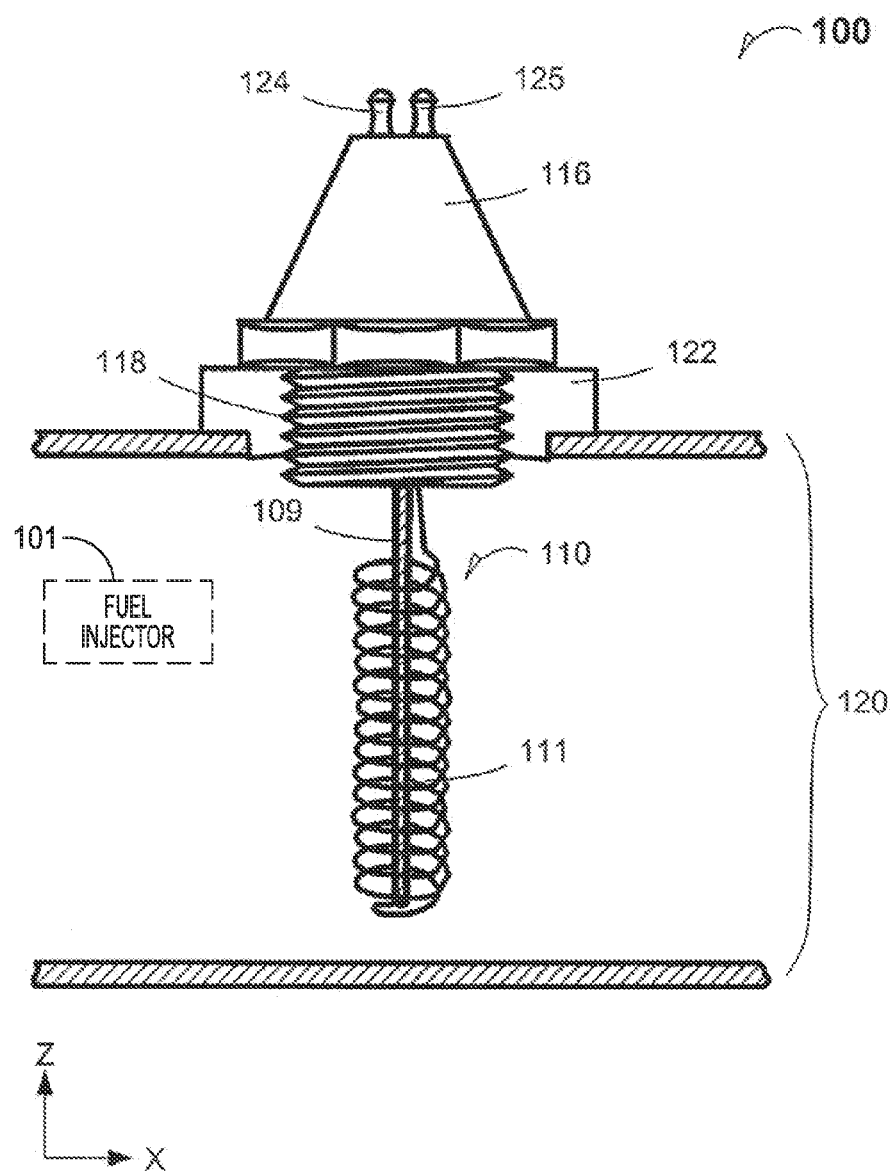
FIG. 1 is an elevational cross-sectional view of a particulate matter (PM) sensor according to an embodiment.

FIG. 1 is an elevational cross-sectional view of a particulate matter (PM) sensor 100 according to some embodiments. The PM sensor 100 includes a probe 110 having an elongate conductive first part 109 and a conductive generally helical coil second part 111 supported by and conductively coupled to a distal end of the first part, axially surrounding at least a portion of the first part 109.

The PM sensor 100 also includes a sensor housing 116 that is physically coupled to and supporting probe 110. In some embodiments an externally threaded fitting 118 supports probe 110 with sensor 100 extending through a wall of an exhaust corridor 120 such as an exhaust pipe or an exhaust manifold to and into an exhaust stream passing through corridor 120. In some embodiments, the exhaust corridor 120 is in the nozzle of a gas turbine.

An internally threaded orifice of sensor mounting 122 welded or otherwise affixed to the exhaust corridor 120, mates with the externally threaded fitting 118 of sensor 100 to support probe 110 in the exhaust stream.

PM sensor 100 is coupled to communicate to the external world through its signal coupling terminal 124 which is conductively coupled to the series connection of elongate first part 109 and helical coil 111 and insulated from sensor housing 116. In some embodiments, an automotive spark plug body is modified to accept and support probe 110. In operation of the sensor, signal coupling terminal 124 will carry significant electrical potentials relative to a reference potential such as the wall of the exhaust corridor 120 as probe 110 measures the electrical characteristics of charged particles in the exhaust stream.

PM sensor 100 may be heated by applying a current through the series connection of elongate first part 109 and helical coil 111 while insulated from sensor housing 116. The heating current is applied through signal coupling terminal 124 and a further terminal 125. In some embodiments heating of the PM sensor drives off carbonaceous material deposited onto the elongate first part 109 or the helical coil second part 111 of probe 110. In some embodiments, heating of the PM sensor anneals the PM sensor with a dielectric coating.

Figure 2:
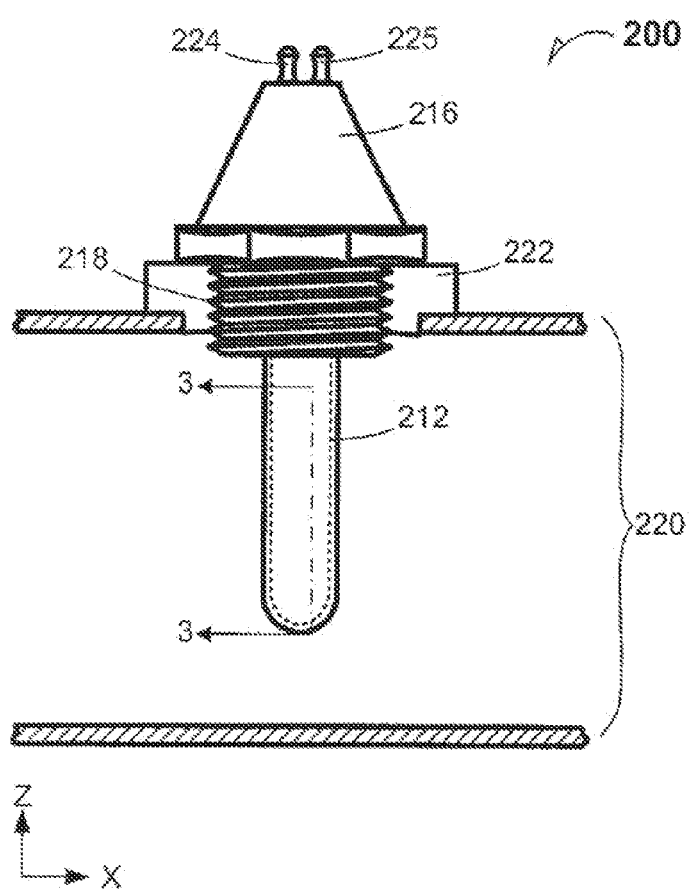
FIG. 2 is an elevational cross-sectional view of a PM sensor according to an embodiment.
Figure 3:
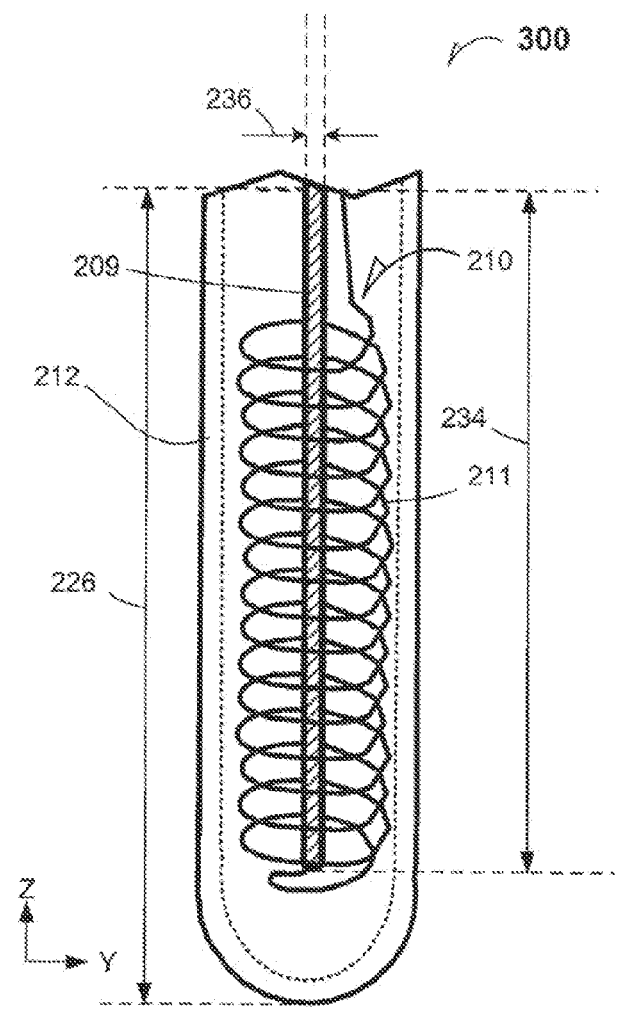
FIG. 3 is a cross-sectional elevational view of a portion of the particulate matter sensor depicted in FIG. 2.

FIG. 2 is an elevational cross-sectional view of a PM sensor 200 according to some embodiments. PM sensor 200 includes a probe 210, shown in more detail in the partially cut-away view in FIG. 3, showing probe 210 suspended within a dielectric protective housing 212 enclosing the portion of the probe to be inserted in the exhaust stream. In an embodiment, the protective housing 212 is a high-temperature dielectric such as alumina. In some embodiments, other materials can be selected such as zirconia or hafnia. In various embodiments, other materials can be selected such as ceria, yttria or ytterbria. In an embodiment, the protective housing 212 is formed by plasma spraying the material onto a mandrel, followed by removal of the mandrel.

The probe 210 may also be referred to as a sensor probe 210. The PM sensor 200 also includes a sensor housing 216 that is physically coupled to and insulated from the probe 210. The coupling may be through an externally threaded fitting 218. The externally threaded fitting 218 may couple to an exhaust corridor 220 such as an exhaust pipe or an exhaust manifold to position probe 210 in the exhaust flow. A sensor mounting 222 is provided that may be welded or otherwise affixed to wall of the exhaust corridor 220 such as with an internally threaded orifice that mates with the externally threaded fitting 218.

The PM sensor 200 communicates to the external world through a signal coupling terminal 224. In some embodiments, a spark plug body can be configured to support the probe 210 and provide the protective housing 212. The signal coupling terminal may carry a significant electrical potential detected by probe 210 when surrounded by an exhaust-gas stream. Heating of the PM sensor 200 to drive off deposited carbonaceous material, or to anneal the PM sensor with a dielectric coating, may be accomplished by connection to a source of electrical power through a terminal 224 and a resistive-heating connector terminal 225.

FIG. 3 is a detailed cross-sectional elevational view 300 of a portion of the particulate matter sensor 200 depicted in FIG. 2. The view of the particulate matter sensor 200 is taken along the section line 3-3 from FIG. 2. In an embodiment, the probe 210 is made of a stainless steel. In an embodiment, the probe 110 is made of super alloy steel that includes cobalt and vanadium doping. Other metals may be used based upon a given application.

The probe 210 may have various dimensions. In an embodiment, the probe 210 may have a length 234 between about 0.25 inches and about 12 inches. In an embodiment, the probe 210 may have a length 234 in a range from about 3 inches to about 4 inches. The elongate section 209 of the probe 210 may also have a thickness 236 between about 1/32 inch and about 3/8 inch. In an embodiment, the thickness 236 of the probe 210 is about 1/8 inch. Further, the helical coil section 211 of the probe 210 may have a thickness that is equal to the thickness 236 of the elongate section 209. In an embodiment, the helical coil section 211 of the probe 210 may have a thickness that is less than the thickness 236 of the elongate section 209. In an embodiment, the protective housing 212 has a length 226 that exceeds that of the probe 210 in a range from about 1% to about 20%.

Figure 4:
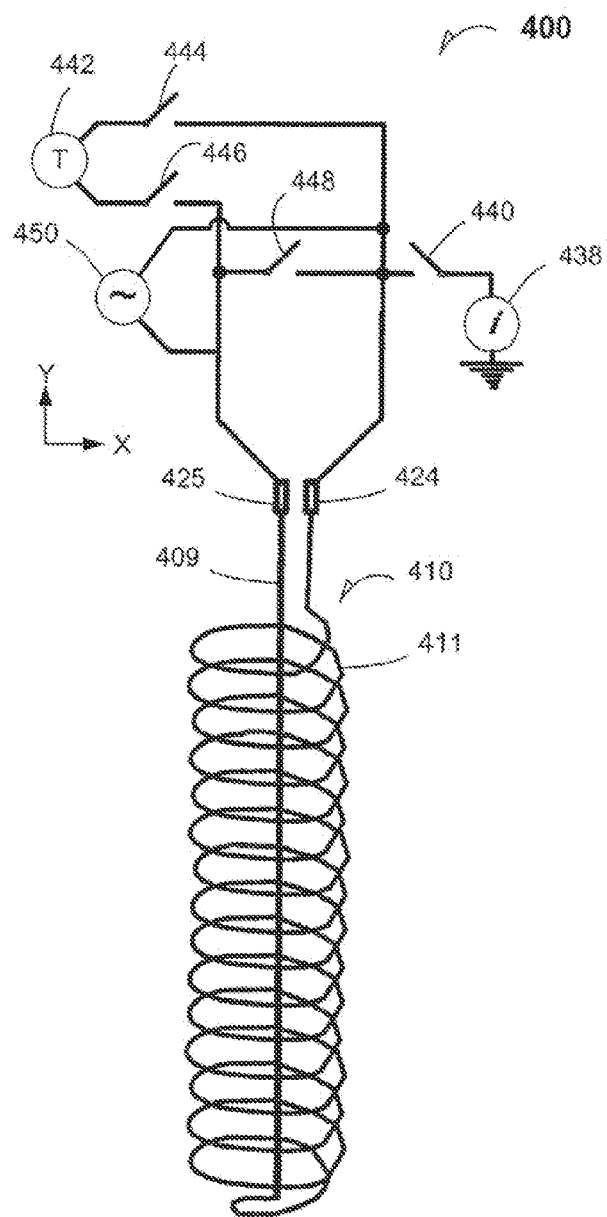
FIG. 4 is a schematic view of the PM sensor connected for operation according to an embodiment.

FIG. 4 is a schematic view the PM sensor in an operating circuit according to an embodiment. A probe 410 includes an elongate first part 409 and a helical coil second part 411. In PM sensing mode, signal coupling terminal 424 is coupled to a current monitor 438 through a closed current-monitor switch 440. A further switch 448 couples terminals 424 and 425 together so that the current through monitor 438 is induced by the induced charge on probe 410 by the charged particles of the exhaust stream flowing over PM probe 410. In some embodiments where the exhaust is in a high-temperature diesel application, the detected current flow is proportional to the particle mass of the particulate matter in the exhaust stream.

In a temperature sensing mode, signal coupling terminal 424 also is coupled to a temperature sensor 442 through temperature-sensor switches 444 and 446. In this mode switches 440 and 448 are open. The temperature sensor measures the temperature of the exhaust stream by measuring the resistance of elongate first part 409 and the helical coil second part 411 which varies in accordance with temperature of the exhaust stream. The temperature sensor probe 410 is useful for diagnostic monitoring of exhaust characteristics that are temperature dependent.

Heating of the sensor 410 is accomplished by applying electrical power through terminals 424 and 425 with switches 440, 444, 446 and 448 open. The conductive path through elongate first part 409 and helical coil second part of probe 410 acts as a heating element when power is applied by supply 450.

Figure 5:
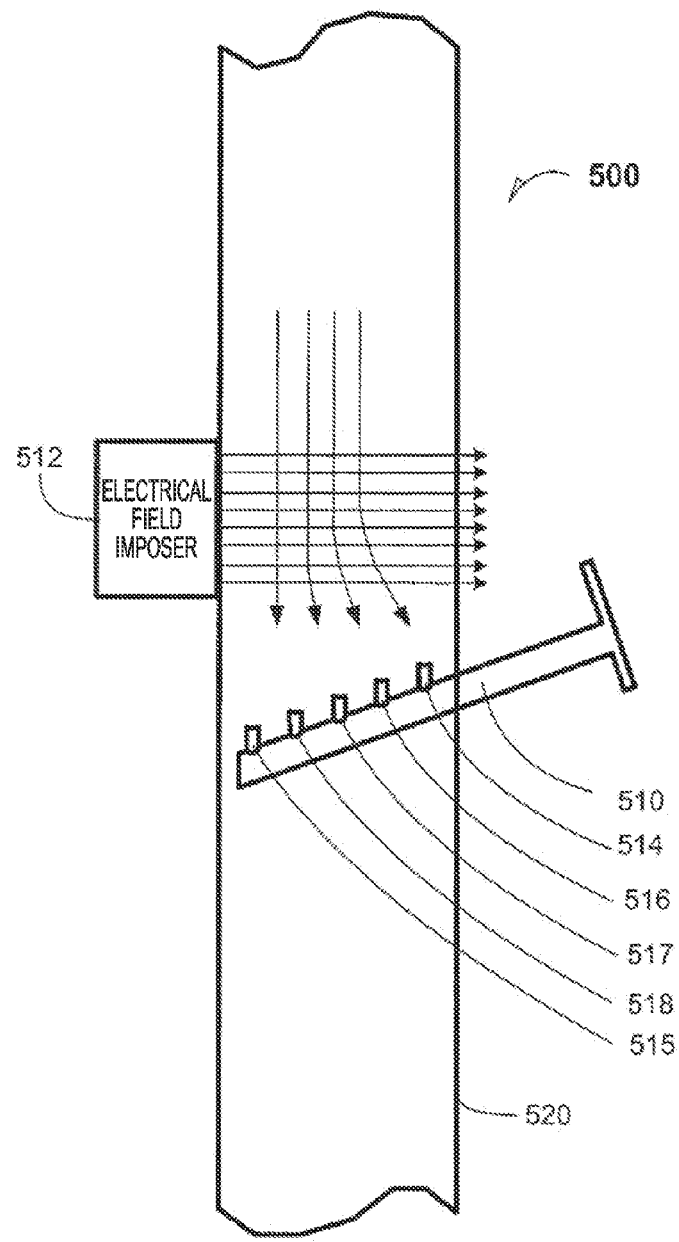
FIG. 5 is a schematic view of a PM classifier, according to an embodiment.

FIG. 5 is a schematic view of a PM classifier 500 according to an embodiment. The PM classifier includes a probe support 510 and an electrical-field imposer 512 which applies an electrical field perpendicular to the flow of the exhaust stream. A first sensor 514 is shown on the probe support 510, and a subsequent sensor 516 is also depicted on the probe support 510. The first sensor 514 and the second sensor 516 each include probes with an elongate first part and a helical coil second part such as the structures depicted in previous FIGS. The probe support 510 is inserted into the exhaust stream in an internal combustion engine exhaust corridor 520. In some method embodiments, the exhaust corridor 520 is an exhaust manifold or an exhaust pipe in a diesel engine. As exhaust particulate matter (EPM) passes through the exhaust corridor 520, the electrical-field imposer 512 imposes is electrical field upon the EPM in a direction perpendicular to its flow. The electrical field acts cause the lightest particulates in the EPM to deflect the most within the exhaust corridor 520, such that the first probe 514 is positioned to detect some of these particulates. Similarly, the electrical field acts to cause the heaviest particulates in the EPM to deflect the least within the exhaust corridor 520, such that the subsequent probe 515 is positioned to detect some of these particulates. In an embodiment, a second probe 516 is positioned adjacent to the first probe 514, such that the next-to-lightest particulates in the EPM to deflect second most within the exhaust corridor 520. Other probes 517 and 518 are depicted according to an embodiment. The number of probes may be selected according to a given application.

Figure 6A:
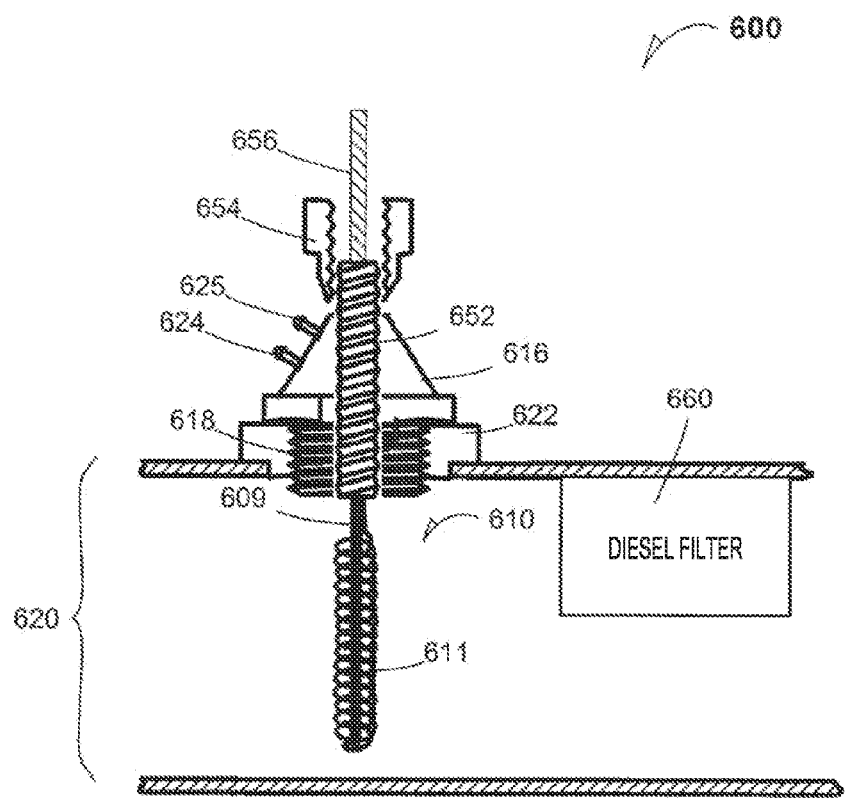
FIG. 6a is an elevational cut-away view of a particulate material sensor according to an embodiment.

FIG. 6a is an elevational cut-away view of a particulate material sensor 600 according to an embodiment. The PM sensor 600 includes a probe 610 including an elongate first part 609 and a helical coil second part 611. The PM sensor 600 also includes a sensor housing 616 that is physically coupled to the probe 610. The coupling may be through an externally threaded fitting 618. The externally threaded fitting 618 may couple to an exhaust corridor 620 such as an exhaust pipe or an exhaust manifold. The exhaust corridor 620 may also be in the nozzle of a gas turbine. A sensor mounting 622 is provided that may be welded or otherwise affixed to the exhaust corridor 620 such as with an internally threaded orifice that accepts the externally threaded fitting 618.

In an embodiment, the probe 610 is retractable by use of a threaded shaft 652 that interfaces with an internally threaded stator 654. The threaded shaft 652 is turned by a torsion shaft 656, such that the interface between the threaded shaft 652 and the internally threaded stator 654, cause the probe to move vertically as depicted in FIG. 6*a*.

The PM sensor 600 communicates to the external world through a signal coupling terminal 624. In an embodiment, an automotive spark plug body may be redesigned to accept the probe 610. In one embodiment, the signal coupling terminal 624 may carry electrical signals indicative of the particulate mass flow detected by probe 610 to allow analysis of the characteristics of an combustion exhaust stream.

Figure 6B:
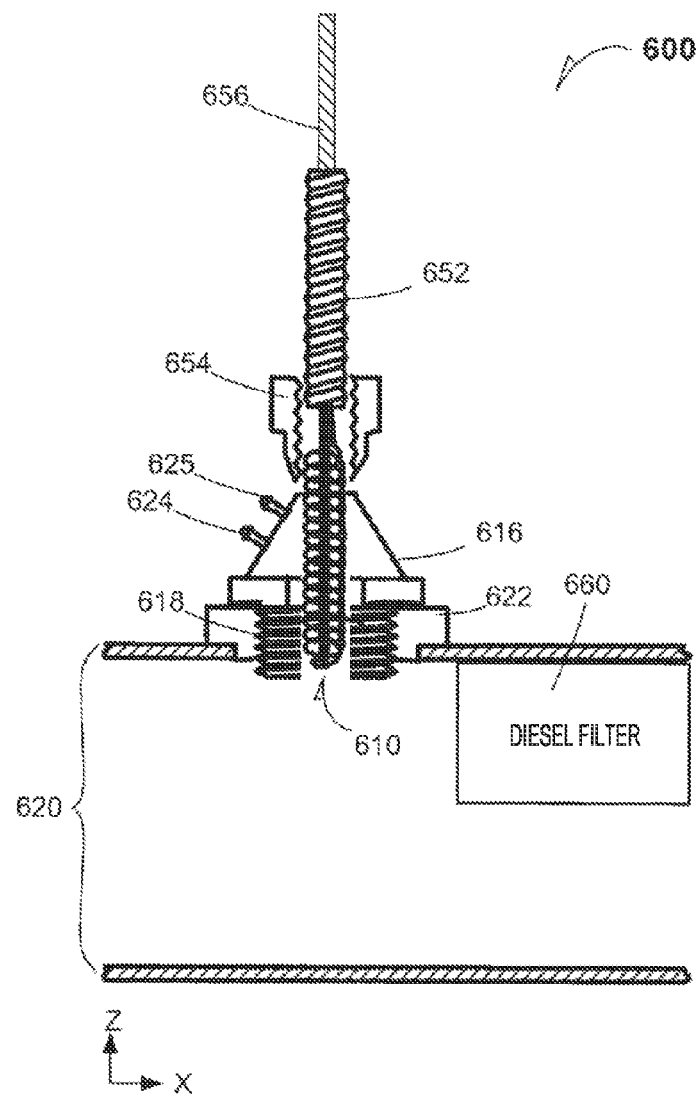
FIG. 6b is a cut-away elevational view of the particulate matter sensor depicted in FIG. 6a during a method of using, according to an embodiment.

FIG. 6*b* is a cut-away elevational view of the particulate matter sensor 600 depicted in FIG. 6*a* during operation of the particulate matter sensor 600, according to an embodiment. In one embodiment, the probe 610 is configured to be moved latitudinally between a deployed position in the exhaust stream (FIG. 6*a*) and a retracted position (FIG. 6*b*) isolated from the exhaust stream. FIG. 6*b* illustrates a PM sensor 600 depicted with the probe 610 retracted out of the exhaust stream. In an embodiment, the probe 610 is retracted during a regeneration cycle such that the probe 610 may be heated by resistance heating and carbonaceous material is driven off the surfaces. Thereafter, the probe 610 may be re-inserted into the exhaust corridor 620 for further use according to the several disclosed embodiments.

During regeneration of diesel particulate filter (DPF) 660, a fuel injector 101 is activated upstream on the exhaust path from sensor 600 by injecting additional heat for the regeneration process. In an embodiment, the probe 610 of sensor 600 is protected during the regeneration of a DPF 660 such as retracting the probe 610 to remove it from extreme conditions during regeneration. In an embodiment, the probe 610 is recalibrated by retracting it from the exhaust corridor 620 and exposing it, while retracted, to a known standard sample such that the response of the probe 610 is recomputed and calibration parameters are updated. Thereafter, the probe 610 is reinserted into the exhaust stream in the exhaust corridor 620 as depicted in FIG. 6*a*.

Figure 7:
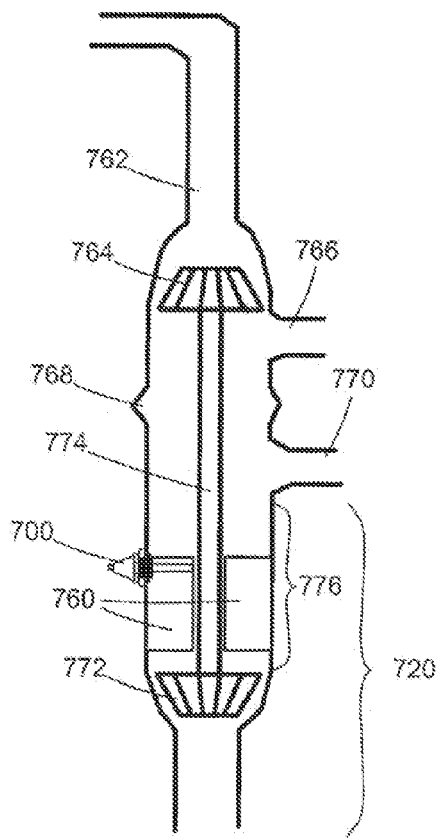
FIG. 7 is a cross-sectional elevational view of a particulate matter sensor and a diesel particulate filter according to an embodiment.

FIG. 7 is a cross-sectional elevational view of a particulate matter sensor 700 and a diesel particulate filter 760 according to an embodiment. An intake manifold 762 leads intake gases to a compressor 764 and to an intake port 766 caused by a seal section 768. After combustion, exhaust gases exit the engine through an exhaust port 770 and pass over a turbine 772 to achieve exhaust power that turns a shaft 774. The shaft 774 turns the compressor. The PM sensor 700 and the DPF 760 are located upstream from the turbine, within the exhaust manifold 776 of the exhaust corridor 720.

By locating the DPF 760 inside the exhaust manifold, particulates that are trapped within the DPF 760, are in a higher temperature range than if the DPF were located downstream from the turbine 772. As depicted, the PM sensor 700 and the DPF 760 are integrated within the exhaust manifold 776 of an internal combustion engine such as a diesel engine. As particulate matter is trapped within the DPF 760 under higher temperature and pressure conditions, the nature of the particulate matter may be related to the conditions of temperature and pressure under which they are trapped within the DPF 760.

In an embodiment, the PM sensor 700 and the DPF 760 are an integral unit as illustrated.

Figure 8:
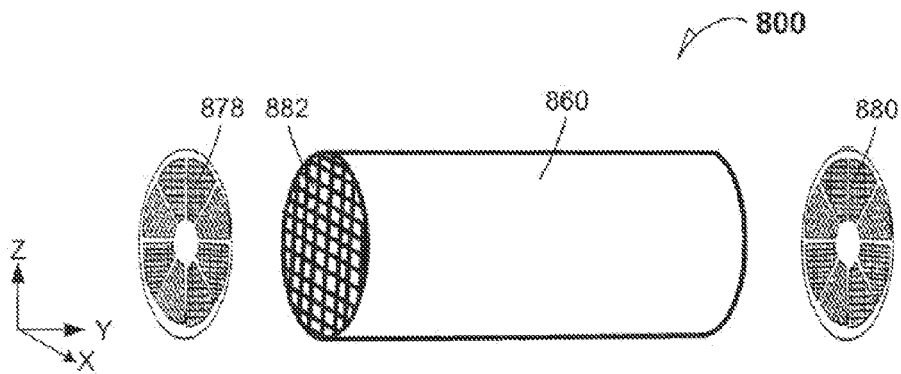
FIG. 8 is an exploded elevational perspective of an upstream electrode for determining failure locations on a diesel particulate filter (DPF) according to an embodiment.

FIG. 8 is an exploded elevational perspective view of a DPF 800 with an upstream deposited electrode 878 and a downstream deposited electrode 880 for determining failure locations within the DPF, according to an embodiment. In DPF 800, a filter cylinder 860 includes a filter medium 882, an upstream electrode 878 and a downstream electrode 880. In one embodiment, the upstream electrode 878 is configured to detect a portion of particulate matter that passes there through. In one embodiment, the downstream electrode 880 is configured to detect a portion of particulate matter that passes there through. In one embodiment, if a given DPF embodiment has a failure anywhere in the filter medium 882, then the detection of the portion of the filter medium 882 having the failure can be localized.

Figure 9:
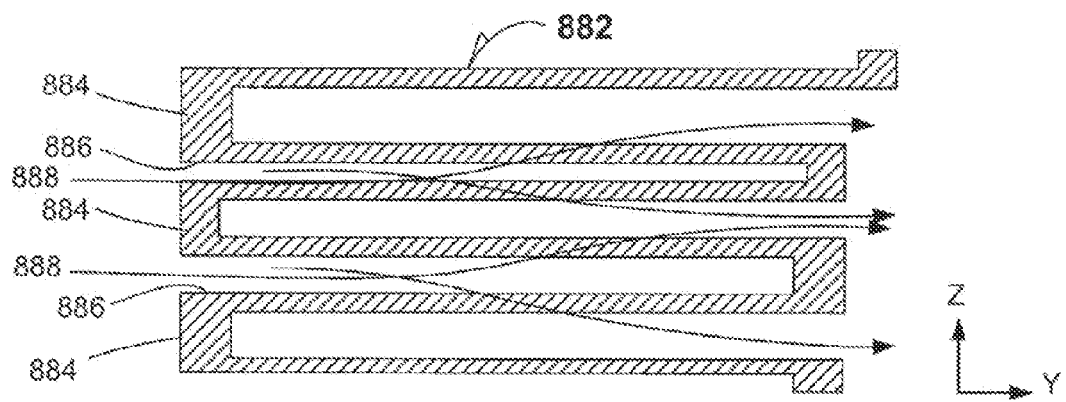
FIG. 9 is a cross-sectional elevational view of a filter medium according to an embodiment.

FIG. 9 is a cross-section elevation view of a filter medium 882 according to an embodiment. The filter medium 882 includes an upstream face 884 and an upstream recess 886. Exhaust gases 888 pass through the filter medium as illustrated.

Figure 10:
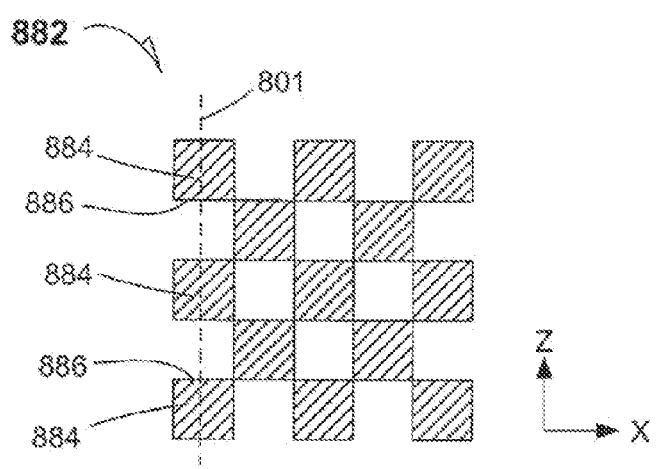
FIG. 10 is a cross-sectional elevational view of the filter medium in a right-angle perspective compared to that depicted in FIG. 9, according to an embodiment.

FIG. 10 is a cross-sectional elevational view of the filter medium 882 in a right-angle perspective compared to that depicted in FIG. 9. A symmetry line 801 illustrates the view seen in FIG. 9 by cross-section.

Figure 11:
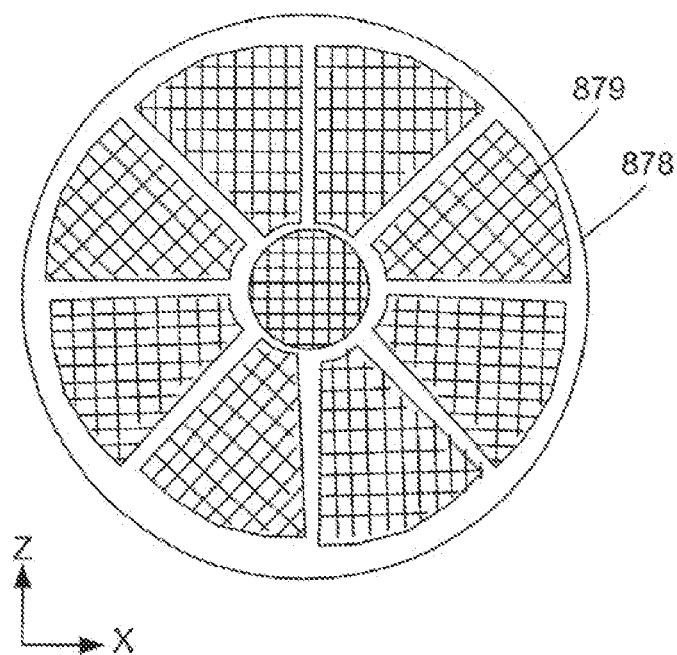
FIG. 11 is a side elevational view of the upstream electrode depicted in FIG. 8, according to an embodiment.

FIG. 11 is a side-elevational view of the upstream electrode 878 depicted in FIG. 8 according to an embodiment. Several electrode sections are depicted, one of which is enumerated with the reference numeral 879.

Figure 12:
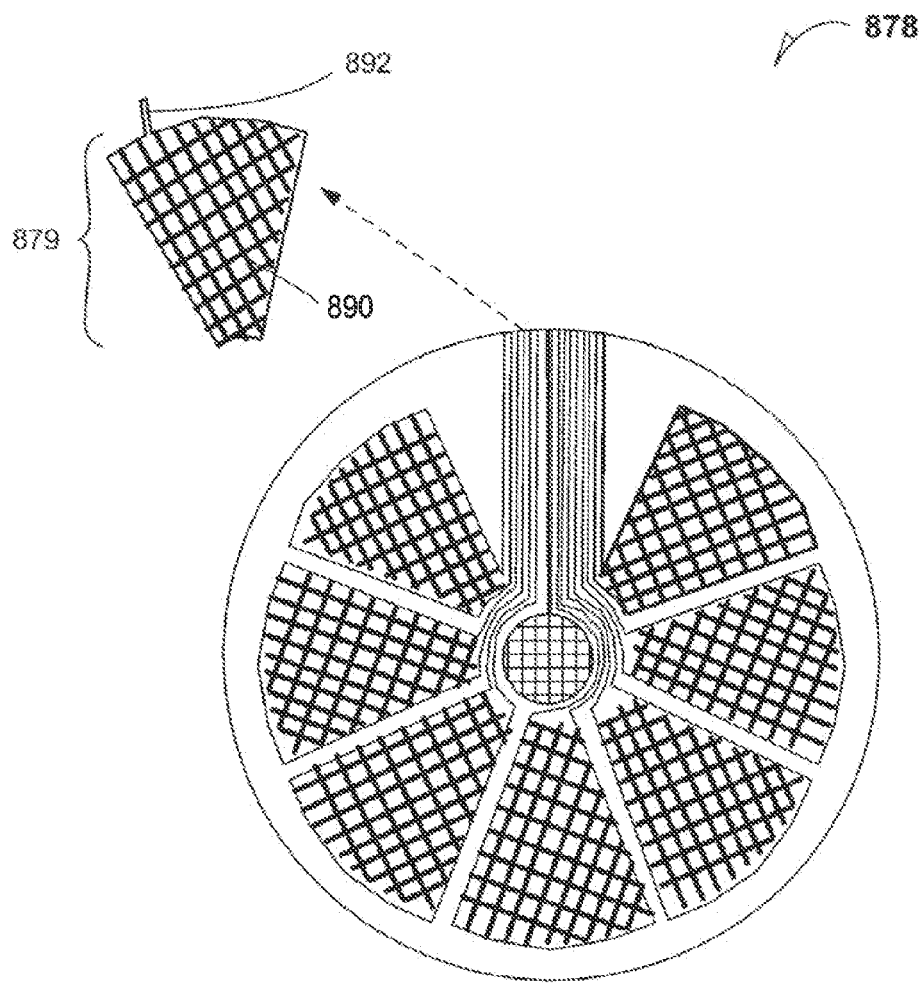
FIG. 12 is a partially exploded side elevational view of the upstream electrode depicted in FIG. 11, according to an embodiment.

FIG. 12 is partially exploded side-elevational view of the upstream electrode 878 depicted in FIG. 11 according to an embodiment. An individual electrode 879 is removed for greater clarity. The electrode 879 includes a mesh area 890 and a pin-out trace 892 for communication to a diagnostic machine. Other electrodes are depicted in FIG. 12, each with a corresponding pin-out trace.

Figure 13:
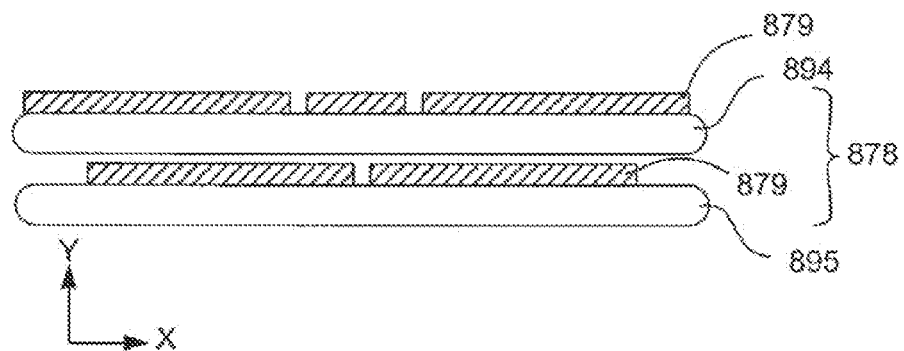
FIG. 13 is a cross-sectional elevational view of the upstream electrode depicted in FIGS. 11 and 12, according to an embodiment.

FIG. 13 is a cross-sectional elevational view of the upstream electrode 878 depicted in FIGS. 11 and 12 according to an embodiment. Where pin-out traces are gathered to a single region at an edge of the upstream electrode 878, the electrode 878 may be constructed with dielectric spacers 894 and 895 such that individual electrodes 879 are electrically isolated.

The location of a failure within a particular longitudinally extending portion of the DPF can be identified using the arrangement shown in FIGS. 8-13. The upstream electrode 878 and the downstream electrode 880 are segmented with similar patterns and a cooperating geometry to restrict and channel the flow of particulate matter into particular longitudinally extending sectors within the DPF. The flow through the downstream grid is measured by determining the charge from particles that pass through the DPF. Because the downstream electrode provides multiple pin out traces 892, the flow for different sections of the DPF can be compared. If the DPF fails through cracking of the monolith making up the DPF, then the increase in the particulate material passing the downstream grid will provide information on the sector in which the failure occurs.

Figure 14:
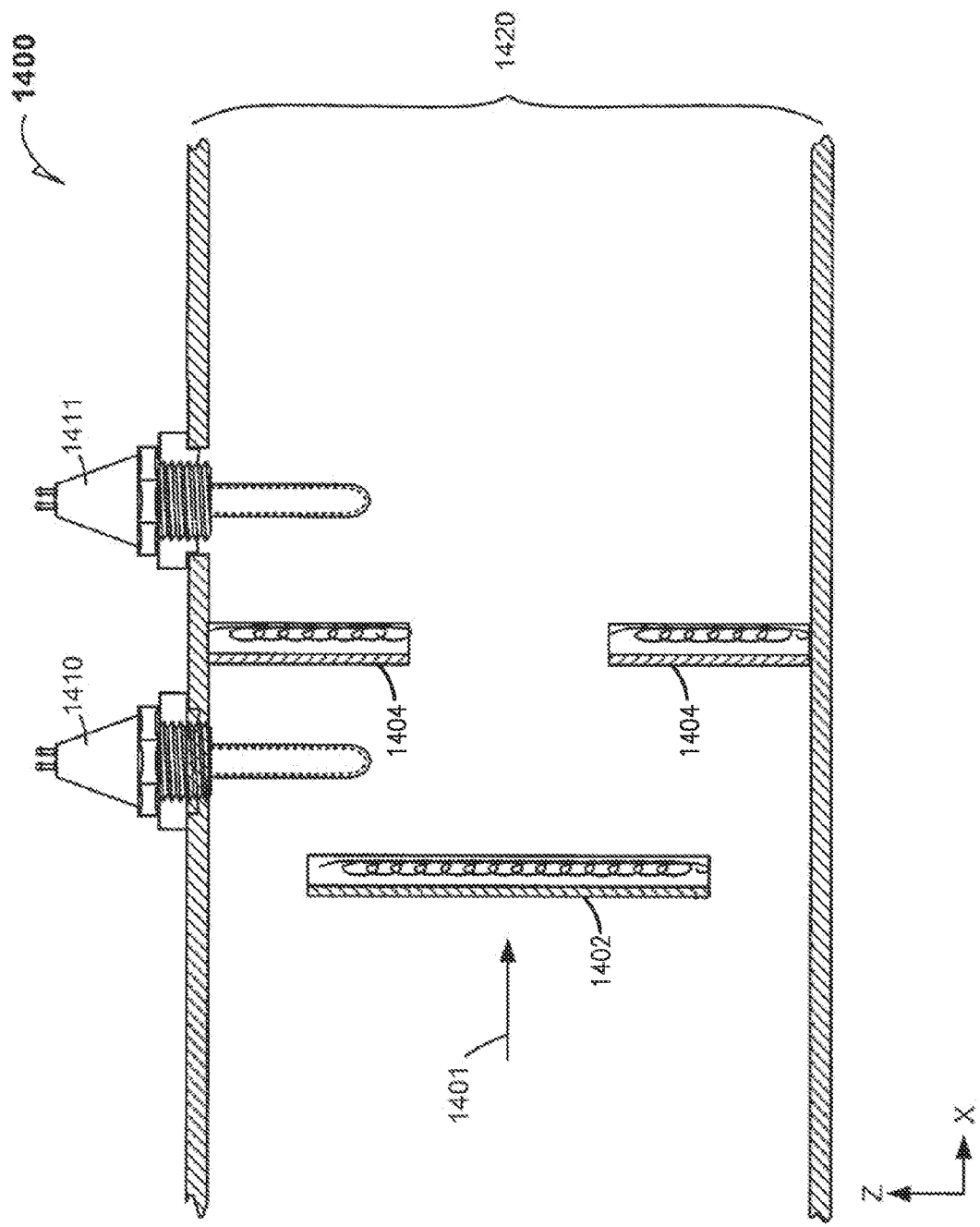
FIG. 14 is a cross-sectional elevational view of a heated impactor and a PM sensor according to an embodiment.

FIG. 14 is a cross-sectional elevational view of an impactor 1400 and PM sensors 1410 and 1411 that provide regeneration by heating according to an embodiment. The impactor 1400 includes a first impactor plate 1402 and a second impactor plate 1404 that each divert the flow 1401 of exhaust gas in an exhaust corridor 1420. The impactor 1400 allows for regeneration by heating the first impactor plate 1402 and the second impactor plate 1404 such that carbonaceous deposits forming on PM sensors 1410 and 1411 can be driven off. The first impactor plate 1402 is configured to be a first heating stage that creates a particle diameter cut that occurs at the transition between the nucleation of soot mode (particles ranging from 5 to 50 nm) and the agglomeration of soot mode (50 to 500 nm). Behind the first impactor plate 1402 and the second impactor plate 1404 are a first PM sensor 1410 and a second PM sensor 1411, respectively.

Figure 15:
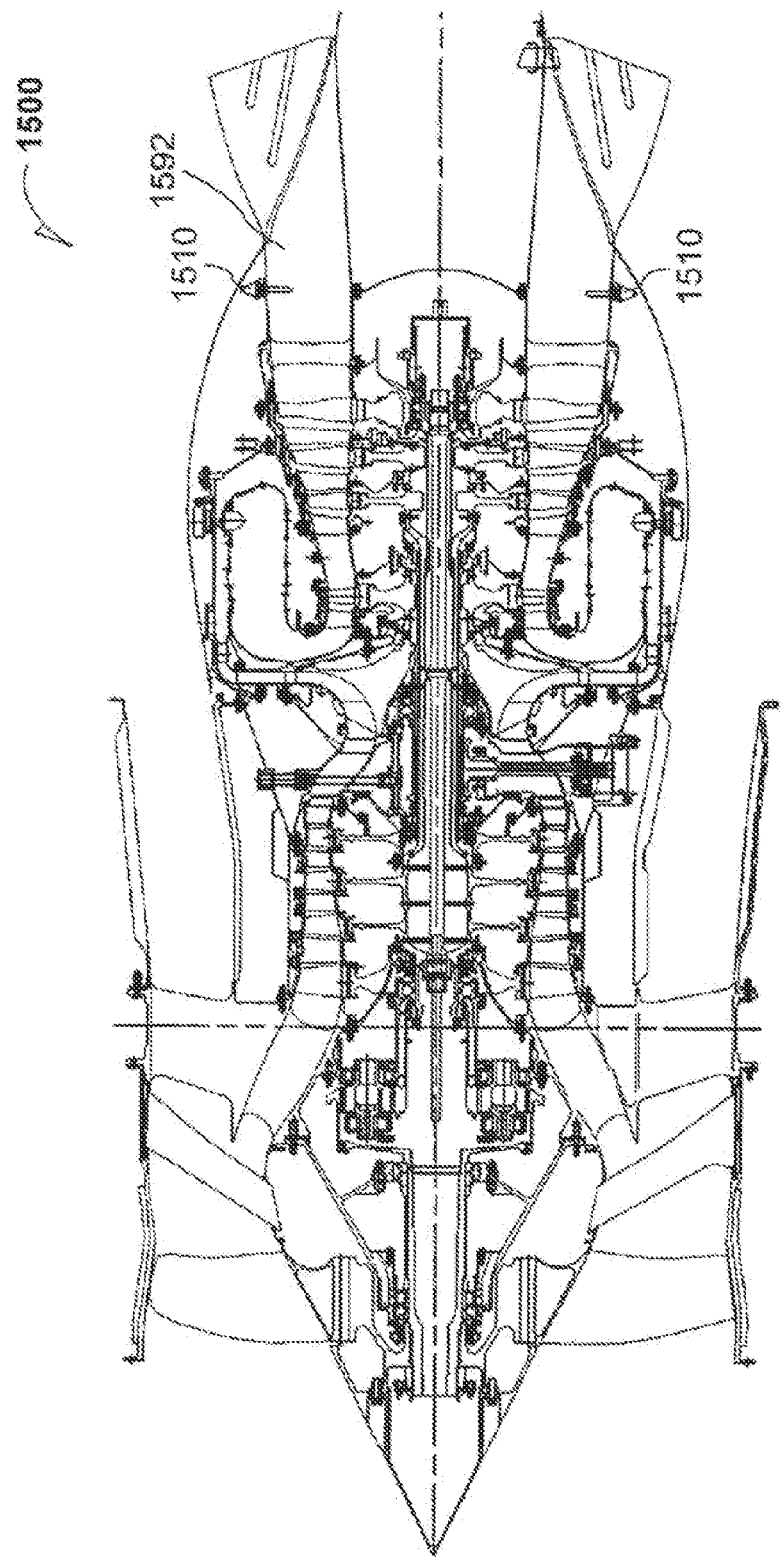
FIG. 15 is a cross-sectional elevational view of a gas turbine with a particulate material sensor according to an embodiment.

FIG. 15 is a cross-sectional elevational of a gas turbine 1500 with a particulate material sensors according to an embodiment. The gas turbine 1500 includes combustor regions 1592 and a PM sensors 1510 is inserted into the cowling which contains the combustor. During combustion, the PM sensor 1510 may detect various particulates.

Figures 16, 17:
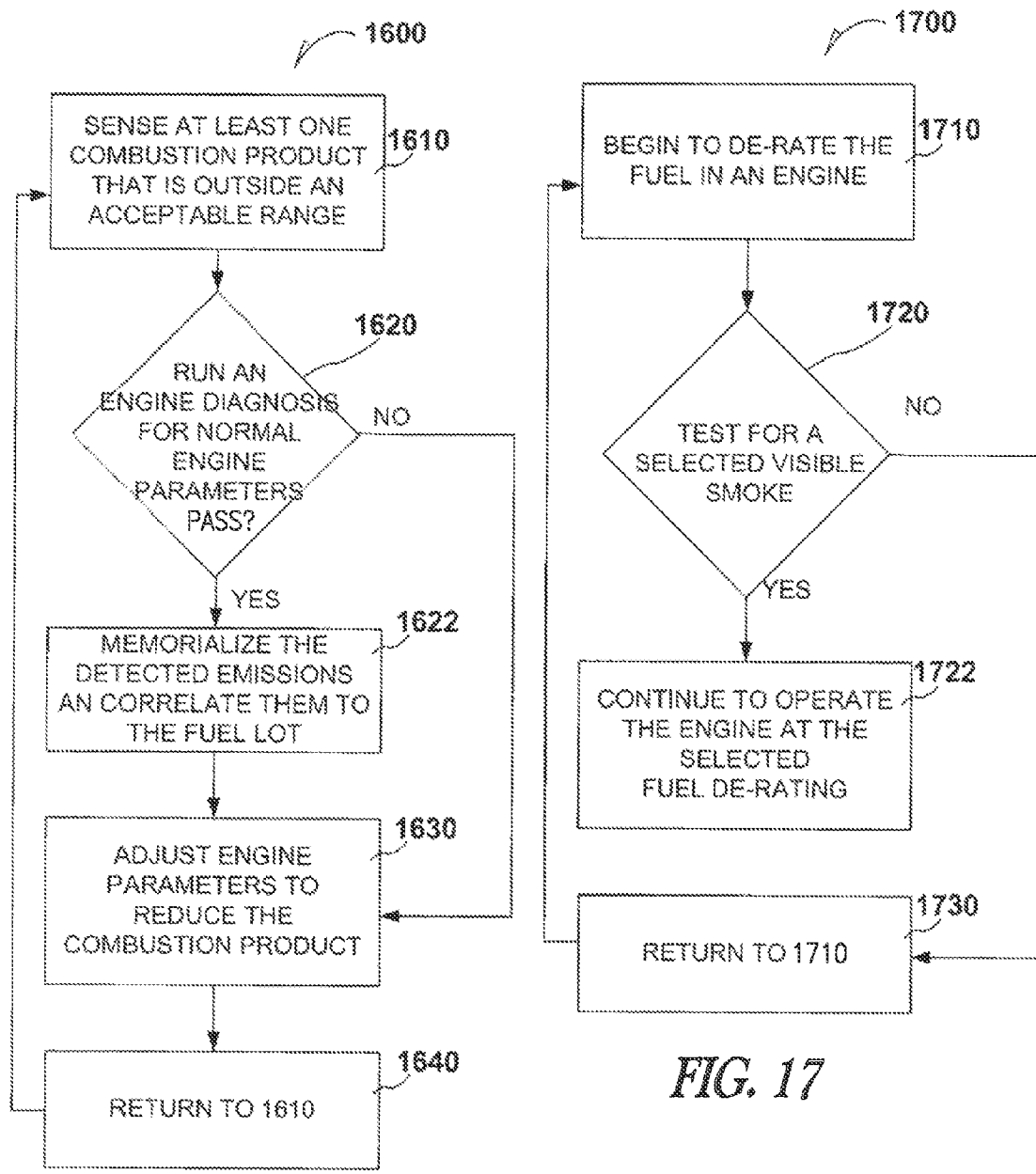
FIG. 16 is a method flow diagram for fuel quality diagnosis according to an embodiment.
FIG. 17 is a method flow diagram that provides for increased stealth operation in an engine, according to an embodiment.

FIG. 16 is a method flow diagram 1600 for fuel quality diagnosis. In order to meet various and changing emission standards, diesel engines need to be fitted with combustion control systems. Also, an after treatment system including particle filters or traps are needed. To make such combustion control systems and after treatment devices reasonably feasible to reduce particulate emissions from an engine, a PM sensor and DPM trap embodiment is used.

Fuel quality is a general term relating to the properties of fuel that contribute to its ability to combust cleanly and efficiently and that may have a more specific meaning as set forth in this disclosure and may relate to the quality and quantity of combustion products emitted under various conditions. In an embodiment, fuel quality refers to the degree of white smoke that is emitted. In an embodiment, fuel quality refers to the degree of soot that is formed during gas-phase combustion. In an embodiment, fuel quality refers to the degree of coke that is formed during liquid-phase combustion, and which also forms a particulate ash. Each of these combustion products may have a bearing on the specific fuel quality.

In an embodiment, instead of analyzing a fuel before it is combusted in an engine such as a diesel or a gas turbine. For example, where an undesirable amount of any aforementioned combustion products are detected by use of a PM sensor or a DPM embodiment, analysis of other engine parameters may be checked. Where the other engine parameters are in a normal or acceptable range, the fuel quality may be inferred to be inferior, or off-specification.

At 1610, the method includes sensing at least one combustion product that is outside an acceptable range. The method includes use of at least one of a PM sensor or a DPM filter. At 1620, the method includes running a diagnosis of engine parameters, and if the engine parameters are in a normal or acceptable range, the fuel quality may be suspected to be off-specification. At 1622, the method includes memorializing the detected emissions and correlating them to the fuel lot.

At 1630, the method includes adjusting engine parameters to compensate for the undesirable combustion products.

At 1640, the method includes returning to 1610 and continuing the process.

FIG. 17 is a method flow diagram 1700 that provides for increased stealth operation in an engine, according to an embodiment. In an embodiment such as a military application or during use of an engine in a situation where visible pollution is to be minimized, control of the combustion may be altered to reduce visible emissions. Particulate material may range in diameter from 0.005 to 0.05 micron (5-50 nm). The particles may consist of metallic compounds, elemental carbon and semi volatile organic and sulfur compounds that form particles during exhaust dilution and cooling. The nuclei mode typically contains 1 to 20 percent of the particle mass and more than 90 percent of the particle number. The accumulation mode particles range in diameter from 0.05 to 0.5 micron (50 to 500 nm). Most of the mass, composed primarily of carbonaceous agglomerates and adsorbed materials, is found here. The coarse mode consists of particles larger than one micron in diameter and contains 5 to 20 percent of the PM mass. These relatively large particles are formed by re-entrainment of particulate matter, which has been deposited on cylinder and exhaust system surfaces.

Particles in the nuclei mode and in the accumulation mode appear to be formed by different mechanisms. Accumulation mode particles are primarily carbonaceous and are associated with rich combustion and poor subsequent oxidation during the engine cycle. On the other hand, most nuclei mode particles are not even formed until the exhaust combustion products dilute and cool. They consist of a complex mix of sulfuric acid and partially combusted fuel and lubricating oil. Formation of these two types of particles likely occurs under different engine operating conditions. One condition is heavy loads favoring carbonaceous accumulation mode particles. Another condition is light loads most likely favoring the formation of vapor phase precursors of nuclei mode particles. The precursors may not undergo gas-to-particle conversion until the exhaust cools and dilutes in the atmosphere.

At 1710, the method includes using at least one of a PM sensor embodiment or a DPF embodiment, to evaluate the particulate matter content of the exhaust stream to allow inferences as to the quality of the fuel and make operating adjustments in view of the quality of the fuel being below the level used to establish the initial operating adjustments. This is referred to as "de-rating" the fuel. In some embodiments, de-rating includes adjusting the operating adjustments in view of the de-rating of the fuel to reduce visible smoke such as white smoke, soot, and ash. At 1710, the method uses an algorithm to seek a de-rating in accordance with the measured particulate output and adjustment such that a visible smoke amount has been reduced to a selected amount, while maintaining acceptable engine performance.

At 1720, the method includes testing for visible smoke data or particulate concentration level and determining if it exceeds a selected amount. If it meets or exceeds the selected amount, the method includes continuing to operate the engine at 1722.

At 1730, the method includes further de-rating the fuel quality and adjusting the operating parameters of the engine to further approach a selected amount of particulate concentration, while maintaining acceptable engine performance. In an embodiment at 1730, a feedback control algorithm may be used. In embodiments where an aircraft engine is in use, the control algorithm may be complex to manage the several engine and aeronautical parameters within acceptable performance margins as the fuel quality is de-rated.

Figures 18, 19:
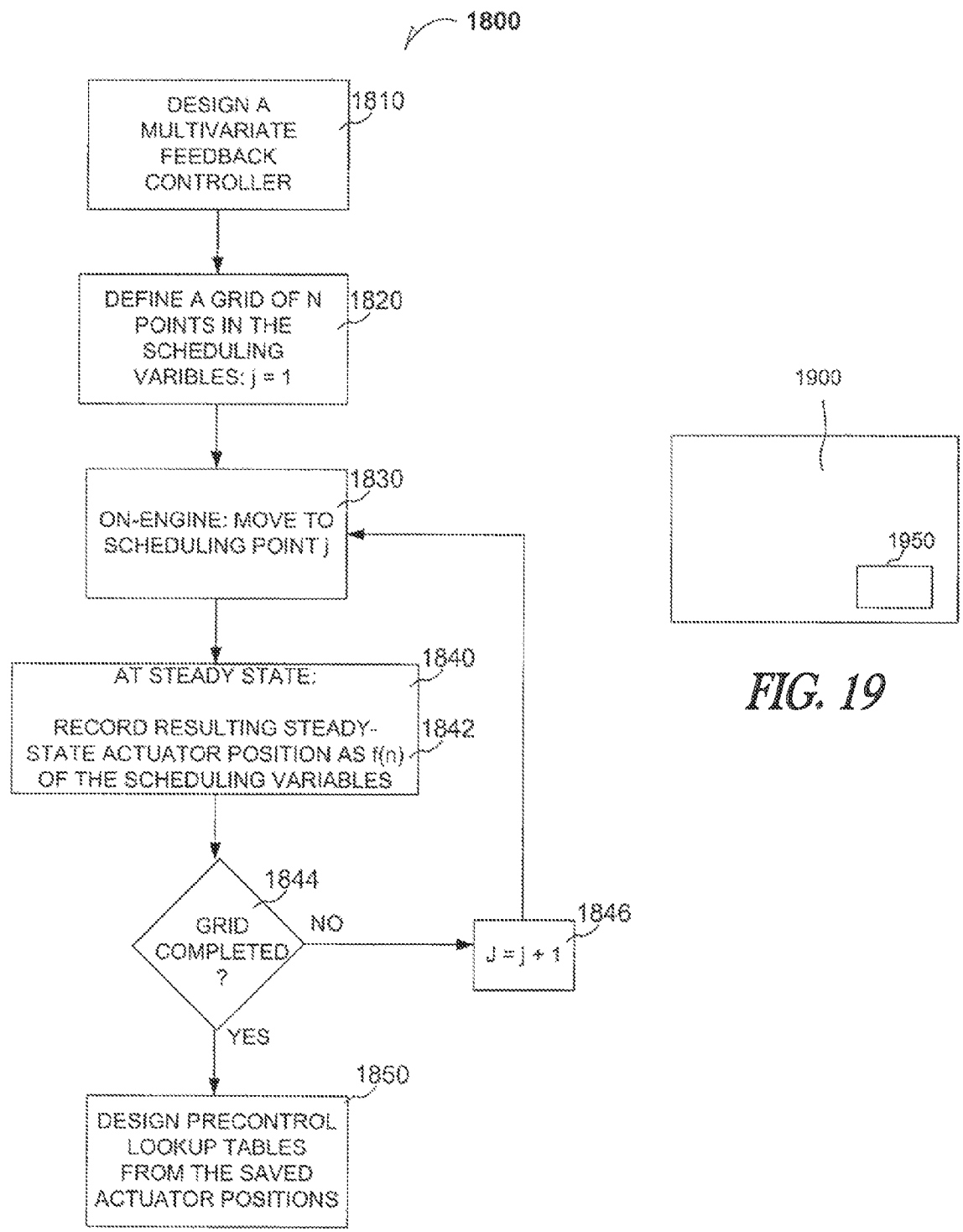
FIG. 18 is a method flow diagram for automatic generation of pre-control lookup tables according to an embodiment.
FIG. 19 is a schematic diagram illustrating a media having an instruction set, according to an example embodiment.

FIG. 18 is a method flow diagram 1800 for automatic generation of pre-control lookup tables according to an embodiment. Once steady-state set points are specified, there remain a limited number of degrees of freedom for engine control, including zero. For full-rank square problems, there are indeed no degrees of freedom remaining. According to an embodiment, multivariable feedback control is used in the calibration process to automatically design pre-control lookup table for actuators in the combustion process.

Because multivariable interactions must be considered during multivariable feedback control design, the process may become significantly time consuming. For example a variable-nozzle turbine (VNT) may need to be control designed to take into account such activities as DPF regeneration and exhaust gas reduction (EGR) goals. Further, actual heat build-up (HACT) may further complicate the multivariable feedback control system, as it can perturb each other variable, and even cause interactions between two non-HACT variables. The actual heat build-up is determined by taking an instantaneous heat build figure from a look-up table, which includes, as its independent variables, engine load and speed. Alternatively, engine load or engine speed may be used as the sole variable for determining heat build-up. The periodically determined heat build-up derived from the lookup table as a function of engine load and/or speed is added to a previously determined value of heat-up to get a summed total heat build-up for the period of operation under consideration.

In an embodiment, a specific number, N, of grid points for on-engine control is multiplied by the time, t, required to reach steady state for each control variable. In an embodiment, the control variables include DPF efficiency as disclosed herein. In an embodiment, the control variables include PM quantities, sizes, and types. Consequently, the PM sensor embodiments and the DPF embodiments are used in the multiple variable pre-control lookup table generation embodiments.

In an embodiment, a 25-by-25 grid is prepared for generating a pre-control lookup table for speed and injection quality for a diesel engine with at least one PM sensor. The generation of a pre-control lookup table with about 15 seconds for each grid location to reach steady state, the time is about 2.6 hours.

In an embodiment, a 12-by-12 grid is prepared for generating a pre-control lookup table for speed and injection quality for a diesel engine with at least one PM sensor. The generation of a pre-control lookup table with about 15 seconds for each grid location to reach steady state, the time is about 36 minutes. Consequently, where a smaller grid, e.g. 12-by-12 is used, a larger grid, e.g. 16-by-16 is used as an upper time boundary for the 12-by-12 grid pre-control lookup table generation.

It becomes apparent that the time required to generate a given pre-control lookup table according to an embodiment, is more a function of the number of scheduling variables and not the number of pre-control lookup tables.

In an embodiment, a conservative controller is designed with less grid locations in order to achieve a trade-off between less accurate pre-control information, and more stable performance over a wide variety of scheduling parameters.

At 1810, the method includes designing a multivariate feedback controller. In an embodiment, the multivariate feedback controller is conservative as defined herein. For example, local linear process models may be used here where likely non-linear, but much more complex models may be more accurate. Thereafter, local linear controllers may be used to construct a non-linear controller. In other words, linear models are used to operate linear controllers, which are used to construct gain-scheduled controllers.

At 1820, the method includes defining a grid of N points in the scheduling variables, and assigning a counter, j, equal to 1.

At 1830, the method includes an on-engine operation of moving to the scheduling point that corresponds with the counter, j; scheduling point j.

At 1840, steady state is first achieved, and then at 1842, the resulting steady-state actuator positions are recorded as a function of the scheduling variables.

At 1844, a decision is made, by querying whether the grid, N, has been completed. If the answer is "NO", then the method increments the counter at 1846 to j=j+1, and returns to 1830.

At 1850, if the answer is "YES", the pre-control lookup tables are designed from the saved actuator positions.

FIG. 19 is a schematic diagram illustrating a media having an instruction set, according to an example embodiment.

A machine-readable medium 1900 includes any type of medium such as a link to the internet or other network, or a disk drive or a solid state memory device, or the like. A machine-readable medium 1900 includes instructions within and instruction set 1950. The instructions, when executed by a machine such as an information-handling system or a processor, cause the machine to perform operations that include any of the system or method embodiments.

In an example embodiment, a machine-readable medium 1900 that includes a set of instructions 1950, the instructions, when executed by a machine, cause the machine to perform operations including any of the system or method embodiments. In an embodiment, the machine-readable medium 1900 and instructions 1950 are disposed in a module 1900 and are locatable within the engine compartment of the internal combustion engine such as a diesel tractor. In an embodiment, the machine-readable medium 1900 and instructions 1950 are disposed in a module 1900 and are locatable within the cab such as near the firewall of the engine compartment of the internal combustion engine such as a diesel tractor.

Thus, a system, method, and machine-readable medium including instructions for Input/Output scheduling have been described. Although the various system or method embodiments have been described with reference to specific example embodiments, it will be evident that various modifications and changes may be made to these embodiments without departing from the broader scope of the disclosed subject matter. Accordingly, the specification and drawings are to be regarded in an illustrative rather than a restrictive sense.

What is claimed is:

1. Sensor apparatus, comprising:
    a housing;
    a probe mounted to the housing, the probe including an elongate first part and a helical coil second part conductively coupled to each other in series with first and second terminals at opposite ends thereof, the probe to be inserted into an exhaust stream in an exhaust corridor; and
    a circuit coupled to the first and second terminals of the sensor probe, to selectively operate the probe as a temperature sensor in a first mode and as a particulate matter sensor in a second mode.

2. The apparatus of claim 1, further including a dielectric protective housing to enclose the portion of the probe to be inserted into the exhaust stream.

3. The apparatus of claim 1, wherein the circuit is further configured to operate the probe in a third mode wherein the probe is heated by an external electrical source.

4. The apparatus of claim 3, wherein operating the probe in the third mode includes heating the probe to a temperature to drive off carbonaceous material deposited onto the probe from the exhaust stream.

5. The apparatus of claim 3, wherein operating the probe in the third mode includes heating the probe to a temperature to anneal the particulate matter sensor with a dielectric coating from material carried in the exhaust stream.

6. The apparatus of claim 3, wherein operating the probe in the third mode includes heating the probe to a temperature to anneal the particulate matter sensor.

7. The apparatus of claim 3, wherein operating the probe in the third mode includes heating the probe to a temperature to anneal the particulate matter sensor with the probe enclosed in the housing, with the housing disposed between the probe and the exhaust stream, with the probe protected from the exhaust stream.

8. The apparatus of claim 1, further including a diesel particulate filter coupled to the probe to comprise an integrated system configurable within an exhaust corridor that includes an intake compressor and an exhaust turbine, the integrated system configurable in the exhaust stream upstream from the exhaust turbine.

9. The apparatus of claim 1, wherein the probe is configured to be moved perpendicular to the flow of exhaust between a deployed position in the exhaust stream and a retracted position.

10. The apparatus of claim 9, wherein the probe is placed in a known standard sample for calibration when the probe is in the retracted position.

11. The apparatus of claim 9, wherein a diesel particulate filter is positioned downstream of the probe and a fuel injector is positioned upstream of the probe to regenerate the diesel particulate filter when the probe is in the retracted position.

12. The apparatus of claim 11, wherein the diesel particulate filter comprises:
   a filter medium;
   a first composite electrode disposed at an upstream location of the filter medium, wherein the first composite electrode includes a plurality of individual electrodes, each having a mesh area and a pin-out trace; and
   a second composite electrode disposed at a downstream location of the filter medium, wherein the second composite electrode includes a plurality of individual electrodes, each having a mesh area and a pin-out trace, the first and second composite electrodes configured with cooperating geometries to measure particulate matter concentrations entering and exiting selected longitudinally extending sectors of the filter.

13. The apparatus of claim 1, further including a diesel particulate filter, wherein the sensor and the diesel particulate filter are an integral unit and located within the exhaust corridor.

14. The apparatus of claim 1, further including an impactor in the exhaust stream, the impactor is self-heatable to sublimate carbonaceous combustion particulate residue deposited on the probe.

15. The apparatus of claim 1, wherein a plurality of sensor probes are mounted on a support extending perpendicularly across the exhaust stream, each of the probes positioned to engage a portion of the stream displaced from the portion engaged by neighboring probes, the apparatus further comprising:
   an electrical field imposer to apply an electrical field perpendicular to the flow of the exhaust stream, the electrical field deflecting particles in the exhaust stream to particular sensor probes of the plurality of sensor probes in accordance with their mass so that the plurality of probes provides particle size distribution data for the exhaust stream.

16. The apparatus of claim 1, further including a diesel particulate filter coupled to the probe to comprise an integrated system, wherein the integrated system is configurable in an internal combustion engine exhaust corridor, wherein the internal combustion engine includes an intake compressor and an exhaust turbine, and wherein the integrated system is configurable upstream from the exhaust turbine.

17. The apparatus of claim 1, wherein the probe is disposed in the housing.

18. The apparatus of claim 17, wherein the housing is formed of a dielectric.

19. The apparatus of claim 18, wherein the dielectric includes alumina.

20. The apparatus of claim 1, wherein the housing is threaded into the exhaust corridor.

* * * * *